(12) United States Patent
Pandian Shanmuganathan et al.

(10) Patent No.: US 10,881,827 B2
(45) Date of Patent: Jan. 5, 2021

(54) PROVIDING A MASK FOR A PATIENT BASED ON A TEMPORAL MODEL GENERATED FROM A PLURALITY OF FACIAL SCANS

(71) Applicant: KONINKLIJKE PHILIPS N.V., Eindhoven (NL)

(72) Inventors: Praveen Kumar Pandian Shanmuganathan, Monroeville, PA (US); Jonathan Sayer Grashow, Cheswick, PA (US)

(73) Assignee: Koninklijke Philips N.V., Eindhoven (NL)

( * ) Notice: Subject to any disclaimer, the term of this patent is extended or adjusted under 35 U.S.C. 154(b) by 116 days.

(21) Appl. No.: 16/139,247

(22) Filed: Sep. 24, 2018

(65) Prior Publication Data

US 2019/0099573 A1 Apr. 4, 2019

Related U.S. Application Data

(60) Provisional application No. 62/565,304, filed on Sep. 29, 2017.

(51) Int. Cl.

| | |
|---|---|
| *A61M 16/06* | (2006.01) |
| *G06T 17/00* | (2006.01) |
| *G16H 30/40* | (2018.01) |
| *B33Y 50/00* | (2015.01) |
| *G16H 20/40* | (2018.01) |
| *A61B 5/107* | (2006.01) |
| *A61B 5/00* | (2006.01) |
| *G06T 19/20* | (2011.01) |

(52) U.S. Cl.
CPC ....... *A61M 16/0616* (2014.02); *A61B 5/1072* (2013.01); *A61B 5/6819* (2013.01); *A61M 16/06* (2013.01); *A61M 16/0683* (2013.01); *B33Y 50/00* (2014.12); *G06T 17/00* (2013.01); *G16H 20/40* (2018.01); *G16H 30/40* (2018.01); *A61M 2016/0661* (2013.01); *G06T 19/20* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 9,470,911 | B2 | 10/2016 | Fonte |
| 2005/0256686 | A1 | 11/2005 | Stabelfeldt |
| 2010/0189342 | A1 | 7/2010 | Parr |
| 2012/0245962 | A1 | 9/2012 | Smith |
| 2012/0305003 | A1 | 12/2012 | Mark |
| 2014/0352134 | A1 | 12/2014 | Ho |
| 2015/0306330 | A1* | 10/2015 | Richard ............ A61M 16/0605 348/77 |

(Continued)

FOREIGN PATENT DOCUMENTS

| | | |
|---|---|---|
| JP | 2010131091 A | 6/2010 |
| WO | WO2016000040 A1 | 1/2016 |

*Primary Examiner* — Fayyaz Alam
(74) *Attorney, Agent, or Firm* — Michael W. Haas

(57) ABSTRACT

A method for identifying a mask for a patient includes: receiving a plurality of images of a patient's face; analyzing the plurality of images to generate a temporal model of the patient's face, determining a mask for the patient using the temporal model of the patient's face, and identifying the mask to the patient.

17 Claims, 2 Drawing Sheets

(56) References Cited

U.S. PATENT DOCUMENTS

| | | |
|---|---|---|
| 2016/0029716 A1 | 2/2016 | Duncan |
| 2016/0070851 A1 | 3/2016 | Wang |
| 2017/0068121 A1 | 3/2017 | Fonte |
| 2017/0128686 A1* | 5/2017 | Margaria ............... A61M 16/06 |
| 2017/0173289 A1 | 6/2017 | Lucey |
| 2018/0028772 A1* | 2/2018 | Davis ................ A61M 16/0644 |
| 2019/0262567 A1* | 8/2019 | Davis ................ A61M 16/0644 |

* cited by examiner

PROVIDING A MASK FOR A PATIENT BASED ON A TEMPORAL MODEL GENERATED FROM A PLURALITY OF FACIAL SCANS

CROSS-REFERENCE TO RELATED APPLICATIONS

This patent application claims the priority benefit under 35 U.S.C. § 119(e) of U.S. Provisional Application No. 62/565,304 filed on Sep. 29, 2017, the contents of which are herein incorporated by reference.

BACKGROUND OF THE INVENTION

1. Field of the Invention

The present invention pertains to methods for identifying a custom mask for a patient for use in receiving a flow of a treatment gas to the airway of the patient. The present invention also pertains to systems for carrying out such methods.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

Current state-of-the-art systems for creating a "custom" mask for a patient for use in delivering a flow of a treatment gas to the patient use a single 3-dimensional (3-D) scan as input to create a spatial model, which is set as a reference for creating the custom mask. An example of such a 3-D scan 10 of the face of a patient is shown in FIG. 1. In such systems, the user is subjected to a neutral face expression during image acquisition from which the possible face geometry is extracted by determining the location of a plurality of facial landmarks or points (labeled A-W) for mask design. However, such approach fails, as variations in the user's facial geometry in unconstrained poses are not considered during such a neutral scan acquisition. Accordingly, the generated mask does not accommodate to the variations in face geometry resulting from movement of the patient's face, which then becomes a problem with comfort and stability. More particularly, face variations which would commonly occur during sleep are not assessed in such 3-D scans, which makes the custom mask creation more difficult to accommodate the user's actual unconstrained facial geometry.

SUMMARY OF THE INVENTION

As one aspect of the invention a method for identifying a mask for a patient is provided. The method comprises: receiving a plurality of images of a patient's face; analyzing the plurality of images to generate a temporal model of the patient's face; determining a mask for the patient using the temporal model of the patient's face; and identifying the mask to the patient.

Identifying the mask to the patient may comprise providing the patient with a specification of the mask or may comprise providing the patient with the mask.

Receiving a plurality of images may comprise receiving a plurality of 3-D images of the patient's face and analyzing the plurality of images may comprise generating the temporal model from the plurality of 3-D images. The plurality of 3-D images may comprise a sequence of 3-D images captured over time. Analyzing the plurality of images may comprise: determining an expected range of facial geometries expressed by the patient's face; registering the range of facial geometries to create the temporal model; and determining an operating range of facial dimensions of the patient, wherein determining the appropriate mask for the patient based on the analysis of the plurality of 3-D images comprises determining an appropriate mask for the patient based on the operating range of facial dimensions. Determining an expected range of facial geometries expressed by the patient's face may comprise determining the positions of a plurality of facial landmarks in the 3-D images.

Receiving a plurality of 3-D images of the patient's face comprises capturing the plurality of 3-D images with a 3-D scanning device.

The plurality of 3-D images may comprise one or more of the patient's face in a plurality of predetermined poses, the patient's face in a plurality of natural poses, and the patient's face in a plurality of differing expressions.

The temporal model may comprise a range of facial dimensions and geometries of the patient's face and determining a mask for the patient may comprise comparing the range of facial dimensions and geometries to establish an operating range of masks.

Receiving a plurality of images may comprise receiving one or more 3-D images of the patient's face and a plurality of 2-D images of the patient's face. Analyzing the plurality of images may comprise: generating a 3-D spatial model of the patient's face by analyzing the one or more 3-D images; and generating the temporal model of the patient's face by registering the plurality of 2-D images to the 3-D spatial model. The plurality of 2-D images may comprise the patient's face in one or more of: a plurality of predetermined poses, a plurality of natural poses, and a plurality of differing expressions. The method may further comprise: extracting information from the plurality of 2-D images, the information including at least one of: landmarks, orientation, and features; and refining the generated 3-D spatial model using the extracted information.

Receiving a plurality of images may comprise receiving a plurality of 2-D images of the patient's face. Analyzing the plurality of images comprises: generating a plurality of 3-D models from the plurality of 2-D images by using standard photogrammetric techniques or disparity maps; and generating the temporal model of the patient's face by registering the 3-D models. The plurality of 2-D images include images of the patient's face in one or more of: a plurality of predetermined poses, a plurality of natural poses, and a plurality of differing expressions.

Receiving a plurality of images comprises receiving a plurality of 2-D images of the patient's face which each contain a reference object of known size and analyzing the plurality of images may comprise generating the temporal model of the patient's face using the plurality of 2-D images.

Receiving a plurality of images comprises receiving a plurality of 2-D images of the patient's face, wherein each 2-D image was captured with a known distance between a device used to capture the 2-D image and the patient's face; and wherein analyzing the plurality of images may comprise generating the spatial and temporal models of the patient's face using the plurality of 2-D images.

As another aspect of the present invention, a system for identifying a mask for a patient is provided. The system comprises: a processing unit; and an output device in communication with the processing unit, wherein the processing unit is programmed to: receive a plurality of images of the patient's face; analyze the plurality of images to generate a temporal model of the patient's face; determine a mask for the patient using the temporal model of the patient's face; and identify the mask to the patient via the output device. The output device may comprise a 3-D printer.

The system may further comprise an image capturing device in communication with the processing unit, the image capturing device structured to capture the plurality of images of the patient's face. The image capturing device may comprise a 3-D scanner.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
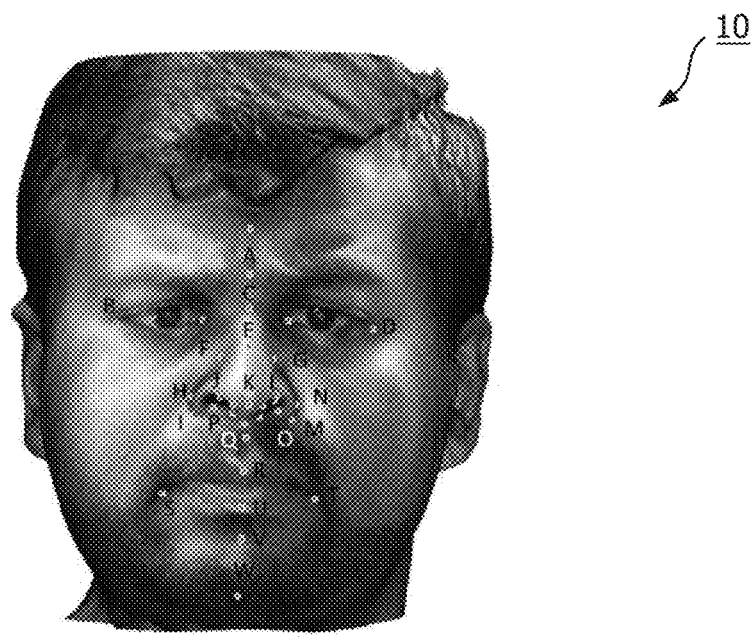
FIG. 1 is an example of a 3-D facial scan obtained in accordance with a prior art approach for mask selection.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled"

means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. As used herein, the term "facial landmark" shall refer to particular points on a human face associated with elements of the face. Examples of facial landmarks may include, without limitation, a point at the tip of the nose; points at edges of the eyes or mouth, etc.

As used herein, the term "temporal model" shall refer to a numeric representation of an object which includes both three dimensional information as well as time-based variations thereof. For example, a temporal model of a face includes information regarding positioning of facial landmarks, surface geometry and texture of the face, both with respect to a fixed point as well as relative to other facial landmarks, geometry, or both. As used herein, the term "image" shall refer to a representation of the form of a person or thing. Such representation may be a reproduction of the form or may be in the form of electronic information describing the form.

As used herein, the term "2-D image" shall refer to a two-dimensional representation of the form of a person or thing, whether in electronic form (e.g., such as stored in digital memory) or in visible form (e.g., displayed via an electronic display). A 2-D image may be captured of a physical object by using a digital camera or 2-D scanning device. As used herein, the term "3-D image" shall refer to a three-dimensional representation of the form of a person or thing, whether in electronic form (e.g., such as stored in digital memory) or in visible form (e.g., displayed via a holographic projector). A 3-D image may be captured of a physical object by using a 3-D scanning device.

As used herein, the term "image registration", also referred to as "registering" is the process of aligning two or more images of the same scene. This process involves designating one image as the reference image, also called the fixed image, and applying geometric transformations or local displacements to the other images so that they align with the reference. By applying image registration to a series of 3-D images, time based changes to the 3-D images are readily obtained for use in a temporal model (i.e., a 3-D model also having information regarding changes occurring over time).

In overcoming shortcomings of prior art approaches which utilize a single 2-D or 3-D image for creating "custom mask", embodiments of the present invention utilize series of expressions (i.e. multiple 2-D or 3-D images) to generate a temporal model of the patient's face that includes not only 3-D spatial information but also time-based information in regards there to. With such temporal information, a wide operating range of facial geometries is determined which can then be utilized for designing a custom mask, or selecting a pre-made mask from amongst a plurality of masks, which provides maximum comfort and stability for the patient. Additionally, time-based analysis (e.g., velocity/acceleration of facial landmarks) can indicate the nature of facial movement (i.e., was it a conscious or unconscious movement or was it a facial expression) which can be used as a criteria to predict a normal operating range of facial geometry during sleep.

Figure 2:
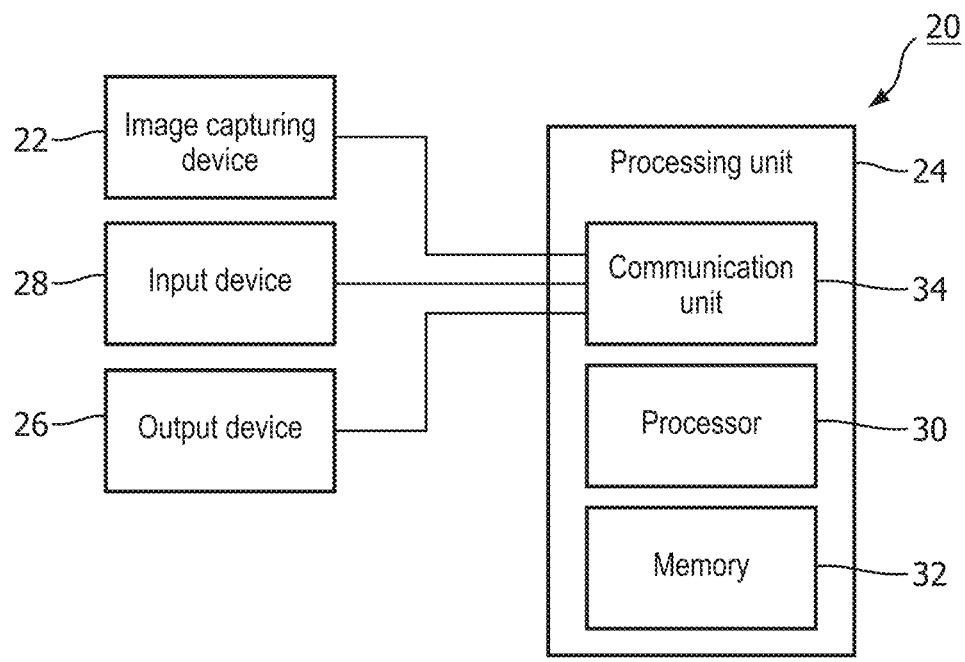
FIG. 2 is a schematic diagram of a system for use in providing a mask for a patient in accordance with an exemplary embodiment of the present invention.

FIG. 2 is a schematic diagram of a system 20 which may be employed in carrying out methods described herein below. System 20 includes an image capturing device 22 for capturing images of a patient's face. As will be appreciated from the examples discussed further herein image capturing device 22 may be one or more of a digital camera structured to capture 2-D images of an object, a scanner structured to capture 3-D scans of an object, or any other suitable device for capturing 2 or 3 dimensional images of an object, which in the present matter would be a patient's face. System 20 also includes a processing unit 24 in communication with image scanning device 22 and an output device 26 in communication with processing device 24. System 20 may also include an input device 28 in communication with processing device 24 for inputting of information to processing unit 24. Alternately, output device 26 may be in the form of a combination input/output device (e.g., without limitation, a touchscreen) for both inputting information to, and receiving information from, processing unit 24.

Processing unit 24 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of system 20.

Processing unit 24 includes a processor 30, a memory 32, and a communication unit 34. Processor 30 may form all or part of a processing portion which may be, for example, a microprocessor, a microcontroller or some other suitable processing device. Memory 32 may form all or part of a memory portion that may be internal to the processing portion or operatively coupled to the processing portion and provide a storage medium for data and software executable by the processing portion for implementing functionality of processing unit 24. Memory 32 can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory.

Communication unit 34 may provide for communication between processing unit 24 and other components of system 20 or other external devices via the internet, cellular, WiFi, wired telephone line, or any other suitable means. For example, without limitation, communication unit 34 may facilitate communication with electronic devices such as a phone, tablet, computer, or other devices whether local or distant, directly or via a network. Communication facilitated by communication unit 34 may allow processing unit 24 to send and/or receive data from the component or device with which it communicates.

Figure 3:
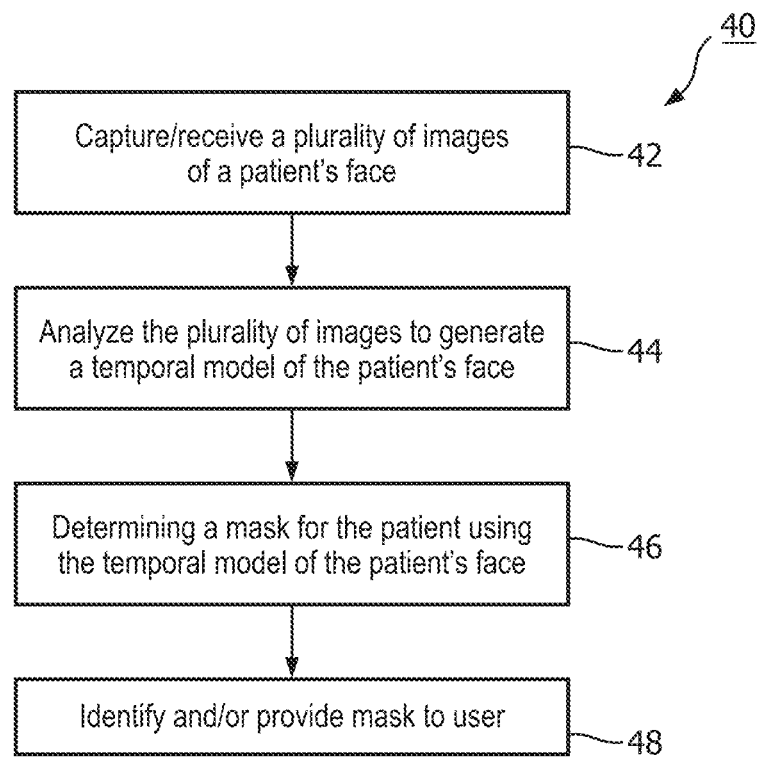
FIG. 3 is a flowchart showing a method for providing a mask for a patient in accordance with an exemplary embodiment of the present invention.

FIG. 3 is a flow chart showing basic steps of a method 40 in accordance with an example embodiment of the present invention, for identifying and/or providing a particular mask for a given patient that could be carried out, for example, without limitation, by all or some the components of system 20. Method 40 begins at 42 wherein a plurality of images of the patient's face are one or both of: captured by an image capturing device such as image capturing device 22 of FIG. 2, or received by processing unit 24 from an outside source which has previously captured such images of the patient's face. The plurality of images may comprise 2-D images, 3-D images, or combinations thereof.

Figure 4:
FIG. 4 is a plurality of 3-D scans of a patient obtained in accordance with an exemplary embodiment of the present invention.

As previously discussed, embodiments of the present invention seek to utilize images which represent ranges of facial geometries of the patient's face. FIG. 4 shows an example of a plurality of such images, labeled A-J, according to an example of the present invention. Accordingly, the plurality of images, regardless of whether they are captured as 2-D or 3-D images, may include the patient's face in a plurality of predetermined poses. Some examples of such predetermined poses may include, for example, without limitation, having the patient pose with an open mouth, a closed mouth, open eyes, closed eyes, looking in various directions, facing in different directions (e.g., left, right, up, down) etc. As another example, the plurality of images may include the patient's face in a plurality of natural poses. Such natural poses may be captured, for example, without limitation, by having the patient generally be themselves without striking any fixed poses while a sequence of images is captured. In yet another example, the plurality of images may include the patient's face in a plurality of differing expressions, for example, without limitation, smiling, frowning, grimacing, pouting, etc.

Next, at 44 the plurality of images or analyzed in order to generate a temporal model of the patient's face. Such generation of a temporal model may be accomplished in various ways depending on the type of images received/captured at 42. For example, in an embodiment wherein a plurality of 3-D images captured over time are utilized, the temporal model may be obtained by registering 3-D images using known image registration methods.

As another example, one or more 3-D images may be utilized along with a plurality of 2-D to generate the temporal model. In such example, a 3-D spatial model of the patient's face is generated using the one or more 3-D images. The temporal model is then generated by registering the plurality of 2-D images to the 3-D spatial model. Additionally, in such example, information extracted from the plurality of 2-D images, including landmarks, orientation, and features, may be used to refine the generated 3-D spatial models.

As yet another example, a plurality of 2-D images may be utilized to generate the temporal model. Such 2-D images may include a reference object of known size or be captured from a device with known distance between the image capture device and the patient's face. 2-D images with known size can be used directly (without ever creating a 3-D spatial model) to create a temporal model that is 2-D+time. The 2-D spatial model can be analyzed in much the same way as the 3D spatial model (e.g. by calculating ranges for the inter-landmark distances). Alternatively, 2-D images of known size could be used to approximate a 3D spatial model, for example by morphing a 3-D template to fit the 2-D images. Alternatively, 2D images could be used to create a 3-D spatial model using any number of techniques known to one skilled in the art such as through the use of disparity maps in the epipolar plane, volumetric deep neural networks (DNN), or generative adversarial network correlations. In another approach, a plurality of 3-D models is generated from the plurality of 2-D images by using standard photogrammetric techniques. The temporal model is then generated by registering the 3-D models.

Once the temporal model has been generated, the temporal model, and more particularly the information regarding the range or ranges of facial expressions contained therein, are used in determining a mask for the patient. Depending on various factors such as, for example, without limitation, time, budget, particular application, such determination may result in determining a design for a custom mask or a determination of an existing mask from amongst a plurality of masks of known sizes and/or geometries.

Finally, 48 the mask is then identified to the patient from amongst the plurality of masks to the patient and/or created, custom mask, and then provided to the patient. As an example, the patient may be provided with information, via any suitable form (e.g., electronically or via hardcopy), particularly specifying the mask (i.e., specifications which particularly identify the mask either from amongst other masks or how to construct from scratch or from components). For example, without limitation, a prescription for obtaining a particular mask or a CAD file or similar item containing instructions and/or dimensional information for constructing a custom mask. Alternatively, the mask may be identified to the patient by providing the patient with the actual mask, be it custom-made or an off-the-shelf item. In the case of a custom-made mask, an output device, such as output device 26 of FIG. 2, in the form of a 3-D printer or other suitable automated manufacturing device may be used to provide the mask to the patient.

From the foregoing, it is to be appreciated that by taking into consideration plurality of facial positions as described in a plurality of 2-D or 3-D images, embodiments of the present invention provide a patient with an all-around better fitting mask than conventional solutions.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. It is also to be appreciated that the overall and/or cross sectional shapes of structures described herein are provided for exemplary purposes only and that such shapes may be varied without varying from the scope of the present invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A method for identifying a mask for a patient, the method comprising:
   receiving a plurality of images of a patient's face;

analyzing the plurality of images to generate a temporal model of the patient's face, the temporal model including both three dimensional information and time-based variations of the three dimensional information;

determining a mask for the patient using the temporal model of the patient's face; and identifying the mask to the patient.

2. The method of claim 1, wherein identifying the mask to the patient comprises providing the patient with a specification of the mask, or the mask.

3. The method of claim 1, wherein receiving a plurality of images comprises receiving a plurality of 3-D images of the patient's face; and wherein analyzing the plurality of images comprises generating the temporal model from the plurality of 3-D images.

4. The method of claim 3, wherein the plurality of 3-D images comprises a sequence of 3-D images captured over time.

5. The method of claim 4, wherein analyzing the plurality of images comprises:

determining an expected range of facial geometries expressed by the patient's face;

registering the range of facial geometries to create the temporal model; and determining an operating range of facial dimensions of the patient, wherein determining the appropriate mask for the patient based on the analysis of the plurality of 3-D images comprises determining an appropriate mask for the patient based on the operating range of facial dimensions.

6. The method of claim 1, wherein the temporal model comprises a range of facial dimensions and geometries of the patient's face; and wherein determining a mask for the patient comprises comparing the range of facial dimensions and geometries to establish an operating range of masks.

7. The method of claim 1, wherein receiving a plurality of images comprises receiving one or more 3-D images of the patient's face and a plurality of 2-D images of the patient's face.

8. The method of claim 7, wherein analyzing the plurality of images comprises:

generating a 3-D spatial model of the patient's face by analyzing the one or more 3-D images; and generating the temporal model of the patient's face by registering the plurality of 2-D images to the 3-D spatial model.

9. The method of claim 8, further comprising:

extracting information from the plurality of 2-D images, the information including at least one: of landmarks, orientation, and features; and refining the generated 3-D spatial model using the extracted information.

10. The method of claim 1, wherein receiving a plurality of images comprises receiving a plurality of 2-D images of the patient's face.

11. The method of claim 10, wherein analyzing the plurality of images comprises:

generating a plurality of 3-D models from the plurality of 2-D images by using standard photogrammetric techniques or disparity maps; and generating the temporal model of the patient's face by registering the 3-D models.

12. The method of claim 1, wherein receiving a plurality of images comprises receiving a plurality of 2-D images of the patient's face which each contain a reference object of known size; and wherein analyzing the plurality of images comprises generating the temporal model of the patient's face using the plurality of 2-D images.

13. The method of claim 1, wherein receiving a plurality of images comprises receiving a plurality of 2-D images of the patient's face, wherein each 2-D image was captured with a known distance between a device used to capture the 2-D image and the patient's face; and wherein analyzing the plurality of images comprises generating the spatial and temporal models of the patient's face using the plurality of 2-D images.

14. A system for identifying a mask for a patient, the system comprising:

a processing unit; and an output device in communication with the processing unit, wherein the processing unit is programmed to:

receive a plurality of images of the patient's face;

analyze the plurality of images to generate a temporal model of the patient's face, the temporal model including both three dimensional information and time-based variations of the three dimensional information;

determine a mask for the patient using the temporal model of the patient's face; and identify the mask to the patient via the output device.

15. The system of claim 14, further comprising an image capturing device in communication with the processing unit, the image capturing device structured to capture the plurality of images of the patient's face.

16. The system of claim 15, wherein the image capturing device comprises a 3-D scanner.

17. The system of claim 14, wherein the output device comprises a 3-D printer.

* * * * *